United States Patent [19]

Zsuga et al.

[11] Patent Number: 5,324,523
[45] Date of Patent: Jun. 28, 1994

[54] CONTROLLED RELEASE PHARMACEUTICAL PREPARATION AND PROCESS FOR PREPARING SAME

[75] Inventors: Miklos Zsuga; Tibor Kelen; Jozsef Nagy, all of Debrecen; Judit Barkanyi, Tiszavasvari; Magdolna Bene, Tiszavasvari; Sandor Ondi, Tiszavasvari; Imre Gulyas, Tiszavasvari; Istvan Gyöker, Tiszavasvari; Janos Repasi, Tiszavasvari; Agota Repasi, Tiszavasvari, all of Hungary

[73] Assignee: Alkaloida Vegyeszeti Gyar, Tiszavasvari, Hungary

[21] Appl. No.: 722,490

[22] Filed: Jun. 27, 1991

[30] Foreign Application Priority Data

Jun. 27, 1990 [HU] Hungary .................. 4007/90

[51] Int. Cl.⁵ .............. A61K 9/14; A61K 9/22
[52] U.S. Cl. .................. 424/486; 424/422; 424/465; 424/468; 424/469; 424/484; 424/600; 424/641; 424/646; 424/682; 424/435; 424/436; 424/423; 514/772.3; 514/953; 514/965; 514/944
[58] Field of Search ............. 424/484, 486, 465, 468, 424/469

[56] References Cited

U.S. PATENT DOCUMENTS

| | | | |
|---|---|---|---|
| 4,177,256 | 12/1979 | Michaels et al. | 424/432 |
| 4,237,114 | 12/1980 | Cardarelli | 424/419 |
| 4,663,147 | 5/1987 | DePrince | 424/486 |
| 4,761,289 | 8/1988 | Shalati et al. | 424/468 |
| 4,830,860 | 5/1989 | Ranade | 424/486 |
| 4,913,906 | 4/1990 | Friedman et al. | 424/469 |

*Primary Examiner*—Thurman K. Page
*Assistant Examiner*—James M. Spear
*Attorney, Agent, or Firm*—Herbert Dubno; Jonathan Myers

[57] ABSTRACT

Controlled release pharmaceutical preparations are prepared by homogenizing an organic or inorganic pharmaceutical active substance such as an opium alkaloid or its salts, an opium antagonist or its salts, an aliphatic or aromatic amine derivative or its salts, a phenolate type medicament, or Zn, Fe, Mg, K, Na salts, a fatty acid or its salt necessary to achieve a continuous phase transfer and an ethylene vinyl acetate copolymer and formulating the resulting homogeneous mixture by a) direct compressing or
b) admixing with a solvent or
c) using a second, auxiliary polymer.

The preparations are suitable for oral or rectal administration or for tissue implantation.

12 Claims, 1 Drawing Sheet

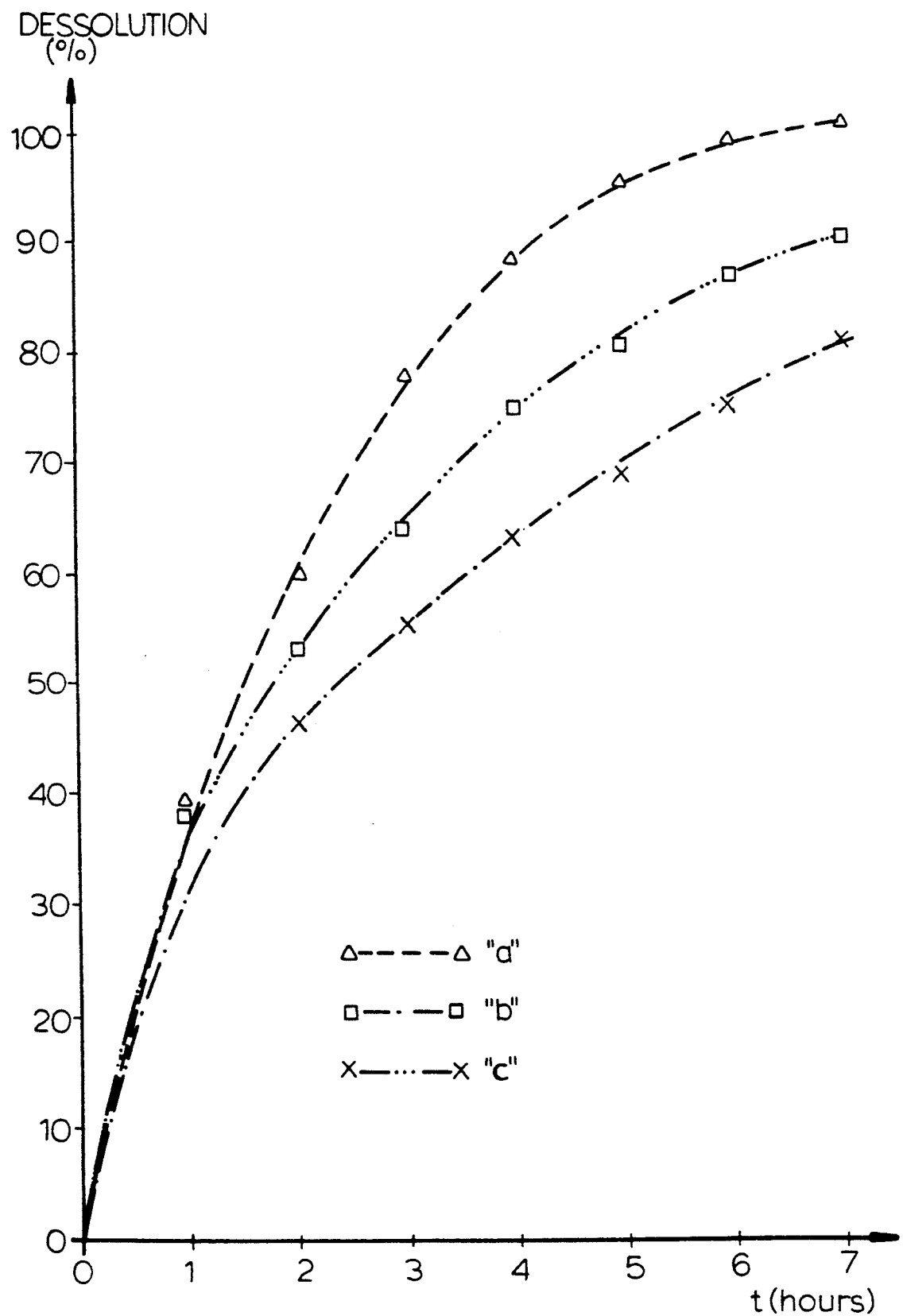

CONTROLLED RELEASE PHARMACEUTICAL PREPARATION AND PROCESS FOR PREPARING SAME

FIELD OF THE INVENTION

The present invention relates to a controlled release pharmaceutical preparation and a process for preparing same.

According to the present invention matrix systems comprising ethylene-vinyl acetate copolymer are provided which are useful for preparing a controlled release preparation containing the active ingredient in ionic form.

BACKGROUND OF THE INVENTION

The medical use of ethylene-vinyl acetate copolymers is well known in the art [Biomaterials 2 201 (1981) J.Biomedical Materials Research 15 267 (1981)]. Controlled release pharmaceutical preparations for treating glaucoma, diabetes as well as controlled release contraceptives were prepared by using this copolymer. Because of its high biocompatibility [J. Biomedical Materials Research 15 267 (1981)] various human applications of this copolymer have been permitted by the FDA.

In view of the above, it is surprising that only a few oral applications are reported in the art and even these are developed for use as a mycoderma adhesive flexible films administered into the mouth cavity [Japanese Kokai Tokkyo Koka JP 6305, 756 8805,756, ibid, 61 93, 113 8693,113, ibid 6354, 318 885 4318] or in dentistry [European Patent Application EP 268464.]

No typical oral application, e.g. use as a base for tablets has been described.

In order to provide a preparation for oral administration we have selected morphine sulphate as an example for the active ingredient because retarding the release of this active substance is essential in analgesic treatment and, on the other hand, this medicament represents a whole family of salt-like active substances with excellent water solubility.

Various polymer systems are proposed for retarding the release of morphine sulphate. For example in J. Pharmacol. Methods 1(2) 21 (1978) and J. Pharm. Sci. 69(8) 980 (1980) dimethylsiloxane, in European Patent Application EP 205 282 a mycoderma adhesive cellulose composition, in French Patent Application Fr. 2,576 213 sulphate and carboxylate anion exchanger, in Rev. Asoc. Esp. Farm. Hosp. 11(1) 111 (1987) PVC and Methacel K-15 M, in ACS. Symp. Ser. 348 (1987) polyethylene oxide and in Br.J. Anaesth 61 221 (1988) cross-linked ethylene oxide are described. According to the above prior art references these polymer systems are suitable for retarding the release of the morphine sulphate but do not ensure simultaneously the wide variability of the dissolution profile and the dissolution rate.

SUMMARY OF THE INVENTION

The present invention is based on the recognition that ethylene vinyl-acetate copolymers can be mixed with both polar and apolar substances without phase separation, by using suitable additives and techniques, due to their ability to undergo double swelling.

As a result, both rate and shape of dissolution can be controlled.

According to the present invention a process is provided for retarding the release of an active substance comprising the steps of homogenizing organic or inorganic pharmaceutical active substances, such as an opium alkaloid or its salts, an opium antagonist or its salts, an aliphatic or aromatic amine derivative or its salts, a phenolate type medicament, or Zn, Fe, Mg, K, Na salts, a fatty acid or its salts necessary for the continuous phase transfer, and ethylene vinyl acetate copolymer and formulating the resulting homogeneous mixture by a) direct compressing or
b) admixing with a solvent or
c) using a second, auxiliary polymer, and by adding conventional pharmaceutical additives into a controlled release dosage form suitable for oral or rectal administration or for tissue implantation.

a) A homogeneous powdered mixture of suitable composition may be pressed simply to a swelling matrix. The dissolution rate and shape can be changed depending on the composition of the powdered mixture.

In order to demonstrate the possibilities of controlling the dissolution rate and shape according to the invention, comparative tests have been carried out with MST 30 mg (Mundidol) retard film tablets. The matrix of Example 1 of the present invention has shown the same dissolution rate and shape (considering the margin of experimental error) as the MST 30 mg (Mundidol) preparation.

b) A uniform powdered mixture of suitable composition mixed with an alcohol gives a gel or pastelike substance which may be formulated by physical methods well known in the art into the desired solid dosage forms.

In accordance with the invention it has been found that both rate and shape of the dissolution can be controlled not only by changing the composition of the powdered mixture, but also by changing the amount of the solvent applied.

c) Since an ethylene vinyl acetate copolymer can be admixed with apolar rubbery substances, such rubbery auxiliary polymers were used in order to achieve forms being stable in biological systems and to avoid the breakdown of said forms.

It has been found that the dissolution rate of e.g. the morphine sulphate depends on the amount of the rubber solution, the ratio of the solvent used for dilution as well as on the time of the triturating. By using a larger amount of the rubber solution, even a retardation of several days is possible. The resulting film makes other types of administration (such as tissue implantation, rectal administering) possible. Natural rubber may be replaced also by different synthetic rubbers. In the case of equal amounts and concentration of rubber solutions the natural rubber shows the slowest dissolution indicating the importance of the molecular weight distribution in controlling the dissolution. A large molecular weight distribution is advantageous.

By using a large amount of solvent, a film is obtained in the course of mixing and subsequent drying which cannot be powdered at room temperature but may be compressed into tablets after appropriate crushing.

The main advantages of the process according to the present invention may be summarized as follows:

1) Due to the amphiphilic properties of the carrier, it is possible to control the release of both organic and inorganic salt-like active substances.

2. The dissolution shape and rate can be varied in a wide range according to the therapeutic needs and can be adjusted exactly.

3. The whole quantity of the active ingredient is set free.

4. The carrier is highly biocompatible.

5. The process can be realized at room temperature, thus it is suitable for retarding substances being sensitive to heat.

6. The process is simple, no special installation is needed, the traditional steps of preparing a pharmaceutical composition may be used.

7. The carrier remaining after dissolution is powdery in cases a) and b) and becomes rubbery after shrinking in case c).

BRIEF DESCRIPTION OF THE DRAWING

The sole FIGURE in this case is a series of three curves where on the X-axis time is plotted in hours and on the Y-axis the percentage of dissolution is plotted for the sustained-release compositions of Examples 1, 2 and 3, respectively designated Tests A, B and C.

The following non-limiting examples illustrate further the invention.

EXAMPLE 1

Morphine sulphate pentahydrate (3.75 g), magnesium stearate (0.55 g) and ethylene vinyl acetate copolymer (Vinnapas Re 530Z, 15.62 g) were homogenized in an agate mortar. The resulting powdered blend may directly be cold compressed into tablets.

EXAMPLE 2

Morphine sulphate (6.0 g), magnesium stearate (1.6 g), cellulose (1.6 g) and ethylene vinyl acetate copolymer (Vinnapas RE 530Z, 10.8 g) were placed into an agate mortar, homogenized and triturated with isopropyl alcohol (6.0 mL). The resulting wet powdered mixture was dried in vacuo at room temperature, while triturating several times. The dried blend may be powdered and compressed into tablets in a desired manner. The dissolution rate can be controlled by the amount of the isopropyl alcohol. When the ratio of powdered blend to isopropyl alcohol was 1:1, the powdered blend could be kneaded to a paste. After drying and applying in an appropriate manner a film was obtained.

EXAMPLE 3 a) Natural rubber (SMR 20 NR, 1 g) was dissolved in toluene (100 mL) under reflux for 24 hours. The resulting slightly yellow solution was cooled and the small quantity of floating solid material was allowed to sediment. Sedimentation can be accelerated by centrifugation. 12 mL of the clear part of the solution was diluted by 10 mL of toluene and the whole quantity was used in the following step.

b) Morphine sulphate (3.05 g), magnesium stearate (0.58 g), cellulose powder (0.44 g) and ethylene vinyl acetate copolymer (Vinnapas RE 530Z, 5.81 g) were placed into an agate mortar and homogenized. The powdered mixture was triturated with the solution prepared according to step a). A wet suspension was obtained which was dried in vacuo while triturating several times. The resulting matrix could be tabletted directly. The dissolution of the active ingredients was tested according to pH. Hg. VII (K/g 15.2.5), in 0.1N HCl, by 100+ l/min rpm. The results are shown in FIG. 1.

We claim:

1. A process for retarding the release of an organic pharmaceutically active substance selected from the group consisting of an opium alkaloid or a pharmaceutically acceptable salt thereof, an opium antagonist or a pharmaceutically acceptable salt thereof, an aliphatic or aromatic amine or a pharmaceutically acceptable salt thereof, and a phenolate medicament or an inorganic pharmaceutically active substance selected from the group consisting of a pharmaceutically acceptable inorganic Zn, Fe, Mg, K and Na salt from a pharmaceutical composition by using ethylene vinylacetate copolymer comprising the steps of homogenizing:

the organic or inorganic pharmaceutically active substance;

a fatty acid containing 10 to 40 carbon atoms or a pharmaceutically acceptable alkali metal or alkaline earth metal salt thereof in an amount necessary to achieve a continuous phase transfer; and an ethylene vinyl acetate copolymer, and formulating the resulting homogeneous mixture by:

(a) direct compressing or (b) admixing with a solvent or (c) using a second, auxiliary polymer, and by adding conventional pharmaceutical additives into a controlled release dosage form.

2. The process for retarding the release of an organic or inorganic pharmaceutically active substance defined in claim 1 wherein the organic or inorganic pharmaceutically active substance is an opium alkaloid or a pharmaceutically acceptable salt thereof or a pharmaceutically acceptable salt inorganic zinc salt and wherein the fatty acid containing 10 to 40 carbon atoms or a pharmaceutically acceptable alkali metal or alkaline earth metal salt thereof is magnesium stearate.

3. A process for retarding the release of a water-soluble organic or inorganic pharmaceutically active substance from a pharmaceutical composition by using ethylene vinylacetate copolymer comprising the steps of homogenizing:

the water-soluble organic or inorganic pharmaceutically active substance;

a fatty acid containing 10 to 40 carbon atoms or a pharmaceutically acceptable alkali metal or alkaline earth metal salt thereof in an amount necessary to achieve a continuous phase transfer; and an ethylene vinyl acetate copolymer, and formulating the resulting homogeneous mixture by:

(a) direct compressing or (b) admixing with a solvent or (c) using a second, auxiliary polymer, and by adding conventional pharmaceutical additives into a controlled release dosage form.

4. A process for retarding the release of an organic pharmaceutically active substance which is an opium alkaloid or a pharmaceutically acceptable salt thereof or for retarding the release of an inorganic pharmaceutically active substance which is a pharmaceutically acceptable zinc salt, from a pharmaceutical composition, by using ethylene vinyl acetate copolymer, which comprises the steps of:

(a) homogenizing the organic pharmaceutically active substance or the inorganic pharmaceutically active substance, magnesium stearate in an amount necessary to achieve a continuous phase transfer, and an ethylene vinyl acetate copolymer to form a homogeneous mixture; and (b) formulating the resulting homogeneous mixture by subjecting same to a cold, direct pressing to form a controlled-release dosage form.

5. The process according to claim 1 variant a) comprising the steps of homogenizing the pharmaceutically active substance, the ethylene vinyl acetate copolymer, the fatty acid or pharmaceutically acceptable salt thereof and the conventional pharmaceutical additives and subjecting the resulting mixture to a cold, direct pressing.

6. The process according to claim 1 variant b) comprising the steps of homogenizing the pharmaceutically active substance, the ethylene vinyl acetate copolymer, the fatty acid or pharmaceutically acceptable salt thereof and the conventional pharmaceutical additives, and mixing the resulting blend with a solvent selected from an alcohol containing 1 to 15 carbon atoms thus obtaining a gel or paste.

7. The process according to claim 6 wherein said gel is formulated into a dosage form for oral or rectal administration or for tissue implantation.

8. The process according to claim 1 variant c) comprising the steps of homogenizing the pharmaceutically active substance, the ethylene vinyl acetate copolymer, the fatty acid or pharmaceutically acceptable salt thereof and the conventional pharmaceutical additives, and mixing the resulting blend with a solution of an auxiliary polymer selected from the group of natural rubbers or a synthetic rubber in an apolar solvent, thus obtaining a gel.

9. The process according to claim 8 wherein said gel is formulated into a dosage form for rectal administration or for tissue implantation.

10. A preparation prepared according to claim 5 for oral or rectal administration or for tissue implantation.

11. A preparation prepared according to claim 7 for oral or rectal administration or for tissue implantation.

12. A preparation prepared according to claim 9 for rectal administration or for tissue implantation.

* * * * *